| United States Patent [19] | [11] | 4,150,132 |
|---|---|---|
| Muller et al. | [45] | Apr. 17, 1979 |

[54] OXADIAZOLOPYRIMIDINE DERIVATIVES

[75] Inventors: Jean-Claude Muller, Rixheim, France; Henri Ramuz, Birsfelden, Switzerland

[73] Assignee: Hoffmann-La Roche Inc., Nutley, N.J.

[21] Appl. No.: 873,182

[22] Filed: Jan. 27, 1978

[30] Foreign Application Priority Data

Feb. 4, 1977 [AT] Austria .................................. 738/77
Dec. 5, 1977 [LU] Luxembourg ........................... 78639

[51] Int. Cl.² .................. A61K 31/505; C07D 498/22
[52] U.S. Cl. .................................... 424/251; 544/255; 544/323; 544/324
[58] Field of Search ........................ 544/255; 424/251

[56] References Cited

U.S. PATENT DOCUMENTS

| 3,769,288 | 10/1973 | Stahle et al. | 544/281 |
| 3,803,148 | 4/1974 | Gibbons | 544/255 |
| 3,816,422 | 6/1974 | Stahle et al. | 544/281 |
| 3,901,928 | 10/1975 | McCall et al. | 544/402 |

Primary Examiner—Paul M. Coughlan, Jr.
Attorney, Agent, or Firm—Jon S. Saxe; George M. Gould; William G. Isgro

[57] ABSTRACT

Alkyl or alkoxyalkyl 5-[3,6-dihydro-1(2H)-pyridyl]-2-oxo-2H-[1,2,4]-oxadiazolo-[2,3-a]primidine-7-carbamates, prepared, inter alia, from the corresponding 6-[3,6-dihydro-1(2H)-pyridyl]-2,4-pyrimidine-dicarbamate-3-oxide, are described. The end products are useful in the treatment of vascular-conditioned hypertension or as vasodilators in the case of peripheral blood supply disorders.

10 Claims, No Drawings

OXADIAZOLOPYRIMIDINE DERIVATIVES

BRIEF SUMMARY OF THE INVENTION

The invention relates to oxadiazolopyrimidines characterized by the formula

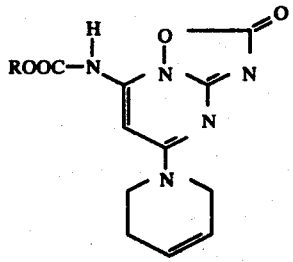

I wherein R is alkyl or alkoxyalkyl, and salts thereof with pharmaceutically acceptable bases. The compounds of formula I are useful in the treatment of vascular-conditioned hypertension, as well as vasodilators in the case of peripheral blood supply disorders.

In another aspect, the invention relates to intermediates of the formulas

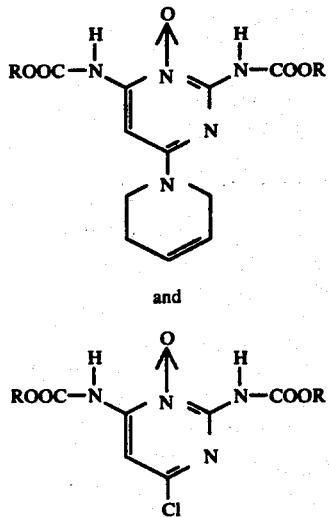

II and

VII wherein R is alkyl or alkoxyalkyl.

DETAILED DESCRIPTION OF THE INVENTION

The oxadiazolopyrimidine derivatives of the invention are characterized by the formula

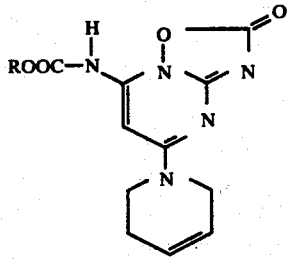

I wherein R is alkyl or alkoxyalkyl, or salts thereof with pharmaceutically acceptable bases.

As used herein, the term "alkyl", alone or in combination, denotes straight-chain and branched-chain saturated hydrocarbon groups containing 1–8 carbon atoms, for example, methyl, ethyl, n-propyl, isopropyl, n-butyl, isobutyl, tert.-butyl, or the like. The term "alkoxy" denotes alkyl ether groups wherein the "alkyl" moiety has the significance earlier described.

Preferred compounds of formula I are those wherein R is alkyl, preferably alkyl of 1–4 carbon atoms. The compound of formula I wherein R is methyl, that is, methyl 5-[3,6-dihydro-1(2H)-pyridyl]-2-oxo-2H-[1,2,4]oxadiazolo[2,3-a]pyrimidine-7-carbamate, is most preferred.

The oxadiazolopyrimidine derivatives of formula I and their salts can be prepared by:

(a) cyclizing a compound of the formula

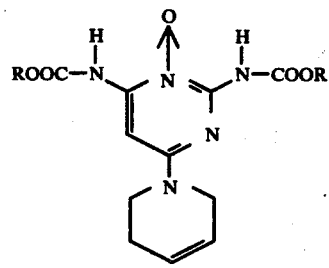

II wherein R is as earlier described, or (b) trans-esterifying a compound of formula I with an alcohol of the formula

R'—OH wherein R' is alkyl or alkoxyalkyl but is different from R, to give a compound of the formula

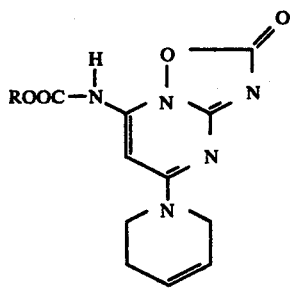

IA wherein R' is as previously described, and, if desired, (c) converting a resulting compound of formula I into a salt or converting a salt into a different salt.

The cyclization of a compound of formula II is carried out in a manner known per se by heating to a temperature in the range of from about 50° C. to about 200° C., preferably in the range of from about 100° C. to about 150° C. The cyclization can be carried out in the absence or presence of a solvent or solvent mixture. If the cyclization is carried out in a solvent or mixture, then aromatic hydrocarbons, such as benzene, toluene, or xylene, chlorinated hydrocarbons, such as chloroform, alcohols, such as butanol or isobutanol, ethers, such as dibutyl ether, dioxane or diethyleneglycol dimethyl ether, dimethylformamide, dimethylsulfoxide, or the like or mixtures thereof, can be used as the solvent. It will be appreciated that either a solvent whose boiling point lies higher than the cyclization temperature or a solvent boiling in the temperature range mentioned earlier at its reflux temperature, can be used. The cyclization is preferably carried out using dimethylformamide or toluene as the solvent. The cyclization time depends on the temperature at which the cyclization is carried out and is in the range of from about 0.25 hour to about 18 hours. If the cyclization is carried out in the preferred temperature range of from about 100° C. to about 150° C., then the cyclization time comprises from about 0.25 hour to about 12 hours, preferably from 0.25 hour to 2 hours. If an alcohol is used as the solvent, then it will be appreciated that, if a trans-esterification is to be avoided, the alcohol must yield a radical which corresponds to that present in the starting material.

In another especially preferred embodiment, the cyclization is carried out in the presence of a base, in which case the temperature can be substantially lower. In this embodiment, the cyclization is preferably carried out at a temperature in the range of from about 0° C. to about 80° C., conveniently at room temperature. Suitable bases are inorganic bases, for example, alkali hydroxides, such as sodium hydroxide, potassium hydroxide, or the like, alkaline earth hydroxides, such as barium hydroxide, calcium hydroxide, or the like, carbonates, such as potassium carbonate, sodium carbonate, or the like, bicarbonates, such as sodium bicarbonate, and organic bases, such as dimethylamine, triethylamine, ethyldiisopropylamine or the like. When a base is utilized, the cyclization is carried out in a suitable inert solvent or solvent mixture. As the solvent there can be used the solvents referred to hereinbefore. When an organic base is utilized, the cyclization is conveniently carried out in a water-containing solvent mixture or in the presence of water in a two-phase system, for example, methylene chloride/water. When it is desired to bring about an intentional trans-esterification, the cyclization is preferably carried out in the presence of a base.

The trans-esterification of a compound of formula I is carried out in a known manner by reacting a compound of formula I with an alcohol at a temperature in the range of from about 25° C. to about 150° C. The trans-esterification is preferably carried out in the presence of a base. Suitable bases for this purpose are alkali alcoholates, alkali hydroxides, carbonates and the like. It will be appreciated that when an alcoholate is utilized, this corresponds to the alcohol used. The trans-esterification is carried out in an inert organic solvent, for example, an aromatic hydrocarbon, such as benzene or xylene, an ether such as dioxane, tetrahydrofuran or ethyleneglycol dimethyl ether, dimethylformamide, dimethylsulfoxide and the like. If the alcohol utilized is liquid at the reaction temperature, then the excess alcohol can also serve as the reaction medium.

The starting materials of formula II are novel and also form part of the present invention. The alcohols can be prepared, for example, by reacting 2,4-diamino-6-[3,6-dihydro-1(2H)-pyridyl]-pyrimidine-3-oxide or the tautomeric 6-amino-4-[3,6-dihydro-1(2H)-pyridyl]-1,2-dihydro-1-hydroxy-2-imino-pyrimidine and 2-amino-4-[3,6-dihydro-1-(2H)-pyridyl]-1,6-dihydro-1-hydroxy-6-imino-pyrimidine of the formulas

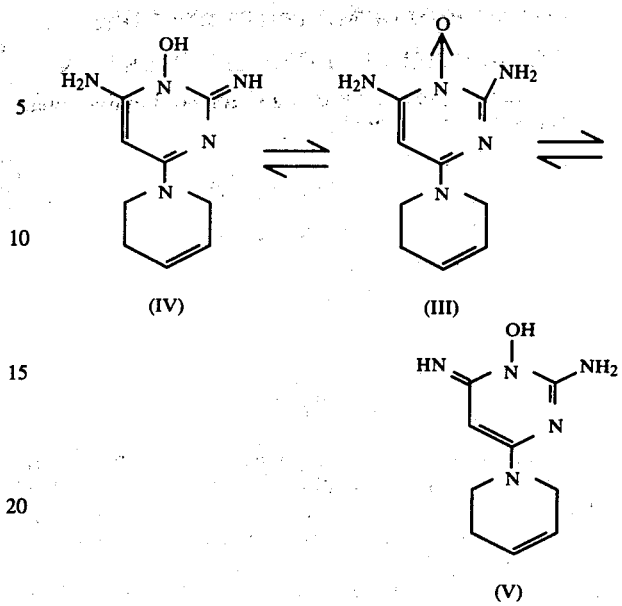

with a chloroformic acid ester of the formula

Cl-COOR            VI wherein R is as previously described.

The reaction is carried out in an inert solvent or solvent mixture in the presence of an acid binding agent. Suitable solvents for present purposes are, for example, chlorinated hydrocarbons such as methylene chloride and chloroform, ethers such as diethyl ether, tetrahydrofuran and dioxane, dimethylformamide and the like, or mixtures thereof. The reaction can also be carried out in a water-containing solvent or in the presence of water in a two-phase system, for example, methylene chloride/water. Examples of acid binding agents are bases such as triethylamine, ethyldiisopropylamine, dimethylamine, pyridine, alkali hydroxides and the like. When the reaction is carried out in the presence of a liquid base, then this can also serve as the solvent. The reaction is conveniently carried out at a temperature in the range of from about −10° C. to about room temperature, preferably in the range of from about 0° C. to about 10° C.

Alternatively, the starting materials of formula II can be prepared by reacting a 6-chloro-2,4-pyrimidine-dicarbamate-3-oxide of the formula

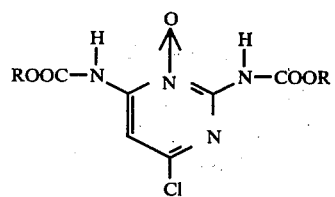

wherein R is as previously described, with 1,2,5,6-tetrahydropyridine.

The reaction is carried out in an inert solvent or solvent mixture. Suitable solvents for this purpose are, for example, chlorinated hydrocarbons such as methylene chloride and chloroform, aromatic hydrocarbons such as toluene, xylene and the like or mixtures thereof. The reaction is preferably carried out under the atmosphere of an inert gas, preferably argon or nitrogen, at a temperature in the range of from about 0° C. to about 50° C., preferably at room temperature. Excess 1,2,5,6-tetrahydropyridine can be used in place of an inert solvent.

The compound of formula III or its tautomers of formulas IV and V can be prepared in an analogous manner to the preparation of known analogous compounds. Two processes are illustrated in the following Formula Scheme. Regarding the precise reaction conditions, reference is made to the detailed Examples which follow.

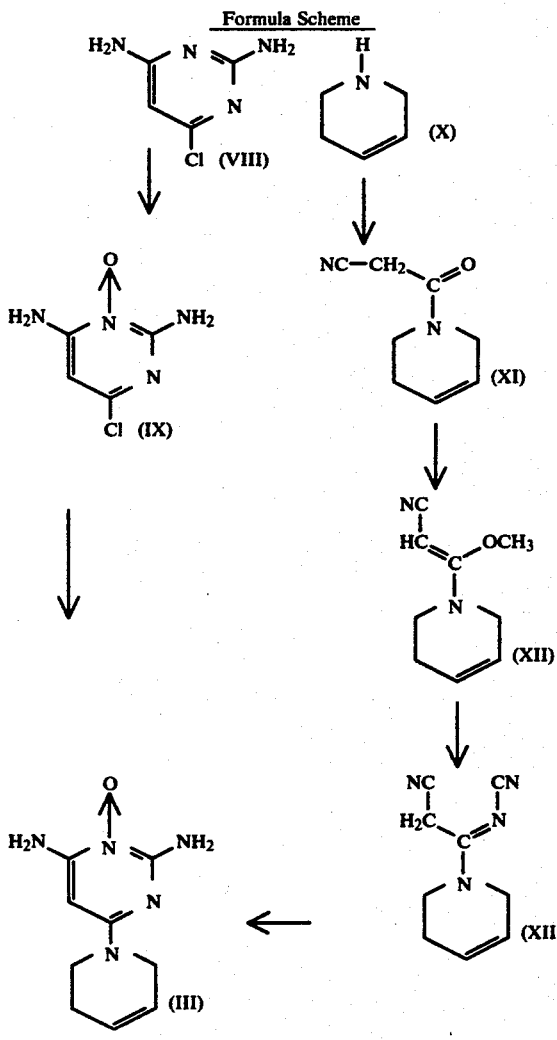

Formula Scheme

The 6-chloro-2,4-pyrimidine-dicarbamate-3-oxides of formula VII are novel and also form part of this invention. They can be prepared by reacting 2,4-diamino-6-chloropyrimidine-3-oxide of formula IX with a chloroformic acid ester of formula VI. The reaction is carried out under the conditions given hereinbefore for the reaction of the compound of formula III or a tuatomer thereof of formula IV or V with a chloroformic acid ester of formula VI.

The compounds of formula I can be converted into salts; for example, by treatment with an inorganic base, for example, an alkali hydroxide such as sodium hydroxide or potassium hydroxide; an alkaline earth hydroxide such as calcium hydroxide; or with an organic base, for example, a monoalkylamine such as methylamine, a dialkylamine such as dimethylamine, a trialkylamine such as triethylamine; a basic amino acid such as arginine; piperidine; an azabicyclooctane or -nonane such as 3-azabicyclo[3.2.1]octane or 3-azabicyclo[3.2.2-]nonane, or the like. Salts of the compounds of formula I can also be prepared by double-decomposition of a suitable salt. The pharmaceutically acceptable salts of the compounds of formula I are preferred.

The oxadiazolopyrimidines provided by the present invention possess long-lasting and desirable vasodilating and/or blood pressure-lowering properties and can, accordingly, be utilized for the treatment of vascular-conditioned hypertensions and also as vasodilators in peripheral blood supply disorders.

The blood pressure-lowering activity of the compounds of formula I can be determined in conscious, spontaneous hypertensive rats by the following method:

The systolic blood pressure and the heart frequency are measured twice before administration of the test substance. The test substance is administered by means of an oesophageal probe twice daily, morning and afternoon. Both parameters are measured 1, 3, 6 and 24 hours after the administration and the percentage variations to the control values are calculated. The systolic blood pressure is measured indirectly in the tail artery of the rat by the method of Gerold et al. (Helv. Physiol. Acta 24: 58–69, 1966; Arzneimittelforschung 18: 1285–1287, 1968).

The vasodilating activity can be determined in conscious, chronic implanted dogs by the following method:

Female cross-bred sheepdogs of about 25 kg. bodyweight are implanted under sterile conditions with an electromagnetic flow probe and a vessel constrictor around the abdominal aorta. The zero-flow is determined by pinching-off the vessel by means of an occluder. The heart frequency, triggered from the pulsating flow, and the aorta flow are continuously recorded during the first three hours after administration of the test substance and after 6, 24, 48 and 72 hours. The dogs in each case lie still, but are not sedated, in an experimentali box for the measurement. The test substances are administered orally in gelatin capsules.

The results obtained are compiled in the following Tables. In each case, the maximum percentage deviation from the control values as well as the duration of activity in hours, calculated as the average value from 5 (rats) or 3 (dogs) experiments, are given.

Table I

| Compound | Dosage mg/kg p.o. | Blood pressure $\Delta\%$ | Duration of activity in hours | Heart frequency $\Delta\%$ | Duration of activity in hours |
|---|---|---|---|---|---|
| A | 1 | −10 | 24 | −11 | >24 |
|   | 3 | −24 | >24 | +9 | >6 |
|   | 10 | −25 | >24 | +22 | >24 |
|   | 30 | −43 | >24 | +22 | >24 |
| B | 1 | −5 | >6 | −16 | >24 |
|   | 3 | −27 | >24 | +16 | >24 |
|   | 10 | −31 | >24 | +16 | >24 |
|   | 30 | −43 | >24 | +23 | >24 |
| C | 3 | +9 | >24 | −5 | >24 |
|   | 10 | −20 | >24 | +12 | >24 |
|   | 30 | −19 | >24 | −7 | >3 |
|   | 100 | −29 | >24 | +16 | >24 |

Table II

| Compound | Dosage mg/kg p.o. | AABF* Duration of activity in | | Heart frequency Duration of activity in | |
|---|---|---|---|---|---|
| | | Δ% | hours | Δ% | hours |
| A | 0.3 | +51 | 48 | +16 | 48 |
| | 1 | +80 | 72 | +21 | <48 |
| | 3 | +206 | >72 | +47 | >72 |
| B | 1 | +29 | 48 | +33 | >48 |
| | 3 | +140 | >72 | +76 | >72 |
| | 10 | +140 | >>72 | +60 | >72 |
| C | 1 | +21 | >24 | +3 | 6 |
| | 3 | +51 | >24 | +8 | 24 |
| | 10 | +88 | >24 | +19 | >24 |
| | 30 | +111 | >48 | +29 | >72 |

A=Ethyl 5-[3,6-dihydro-1(2H)-pyridyl]-2-oxo-2H-[1,2,4]oxadiazole[2,3-a]pyrimidine-7-carbamate
B=Isobutyl 5-[3,6-dihydro-1(2H)-pyridyl]-2-oxo-2H-[1,2,4]oxadiazolo[2,3-a]pyrimidine-7-carbamate
C=Methyl 5-[3,6-dihydro-1(2H)-pyridyl]-2-oxo-2H-[1,2,4]oxadiazolo[2,3-a]pyrimidine-7-carbamate
*AABF=Abdominal Aortic Blood Flow The compounds of formula I and their pharmaceutically acceptable salts can be used as medicaments, for example, in the form of pharmaceutical preparations which contain them in association with a compatible pharmaceutical carrier material. The carrier material can be an organic or inorganic inert carrier material suitable for enteral or parenteral administration, for example, water, gelatin, gum arabic, lactose, starch, magnesium stearate, talc, vegetable oils, polyalkylene glycols, or the like. The pharmaceutical preparations can be made up in solid form, for example, as tablets, dragees, suppositories or capsules, or in liquid form, for example, as solutions, suspensions or emulsions. The pharmaceutical preparations may be sterilized and/or may contain adjuvants such as preserving, stabilizing, wetting or emulsifying agents, salts for varying the osmotic pressure or buffers. The pharmaceutical preparations can also contain still other therapeutically valuable substances.

The daily dosage of a compound of formula I in the case of oral administration can comprise from about 10 mg. to about 500 mg. and in the case of intravenous administration from about 1 mg. to about 50 mg. It will be appreciated that the aforementioned dosages are given by way of examples and can be modified according to the severity of the conditions to be treated and according to the judgment of the person administering a compound of formula I.

The following Examples further illustrate the invention. All temperatures are stated in degrees Centigrade, unless otherwise mentioned.

EXAMPLE 1

Preparation of methyl 5-[3,6-dihydro-1(2H)-pyridyl]-2-oxo-2H-[1,2,4]oxadiazolo[2,3-a]pyrimidine-7-carbamate 50 G. of dimethyl 6-[3,6-dihydro-1(2H)-pyridyl]-2,4-pyrimidine-dicarbamate-3-oxide are heated to 140° C. under an argon atmosphere in 300 ml. of dimethylformamide while stirring for 30 minutes. The dimethylformamide is evaporated under reduced pressure and the residue is recrystallized from methanol/methylene chloride. There is obtained methyl 5-[3,6-dihydro-1(2H)-pyridyl]-2-oxo-2H-[1,2,4]-oxadiazolo[2,3-a]pyrimidine-7-carbamate, having a melting point of 213°-215° C. (decomposition).

The dimethyl 6-[3,6-dihydro-1(2H)-pyridyl]-2,4-pyrimidine-dicarbamate-3-oxide used as the starting material can be prepared as follows:

(A) 144.5 G. of 2,4-diamino-6-chloropyrimidine are suspended in 2000 ml. of ethanol. While stirring, the suspension is warmed to 35° C. (about 15 minutes), the greater part of the substance passing into solution. The mixture is then cooled to 6°-8° C. and, at this temperature, there are added dropwise within the course of 40 minutes 175 ml. of 40% peracetic acid in glacial acetic. After completion of the addition, the mixture is stirred at 6°-8° C. for a further 30 minutes. The mixture is then left to warm up to room temperature and stirred at this temperature for 3 hours. 2000 Ml. of petroleum ether are then added, the mixture is left to stir for 1 hour and then left to stand overnight. The separated precipitate is filtered off, back-washed with 200 ml. of petroleum ether and dried under reduced pressure, there being obtained 2,4-diamino-6-chloroyrimidine-3-oxide. Recrystallization yields analytically pure product, having a melting point of 193° C.

The aforementioned 2,4-diamino-6-chloropyrimidine-3-oxide can also be prepared as follows:

75 G. of 2,4-diamino-6-chloropyrimidine are dissolved in 1500 ml. of ethanol at 35° C. The solution is cooled to −10° C. and a solution of 100 g. of 3-chloroperbenzoic acid in 500 ml. of ethanol is slowly added dropwise in the course of 1 hour. The suspension is subsequently stirred at −10° C. for 7 hours and left to stand at 5° C. overnight. The suspension is neutralized with 24 g. of sodium hydroxide in 100 ml. of water. The solid material is filtered off and recrystallized from ethanol, there being obtained pure 2,4-diamino-6-chloropyrimidine-3-oxide.

155 G. of 2,4-diamino-6-chloropyrimidine-3-oxide are mixed and stirred under an argon atmosphere with 640 ml. of o-xylene and 260 ml. of 1,2,5,6-tetrahydropyridine. The mixture is then heated to reflux for 30 minutes, the internal temperature rising from 115° C. to 123° C. The mixture is then cooled to 5° C., treated with 40 g. of sodium hydroxide in 400 ml. of water and stirred at 5° C. for 1 hour. The precipitate formed is filtered off, washed with 200 ml. of water and recrystallized from 3000 ml. of water, there being obtained pure 2,4-diamino-6-[3,6-dihydro-1(2H)-pyridyl]pyrimidine-3-oxide having a melting point of 263°-265° C. (decomposition).

45 G. of 2,4-diamino-6-[3,6-dihydro-1(2H)-pyridyl]-pyrimidine-3-oxide are mixed in 600 ml. of methylene chloride with 90 ml. of triethylamine and cooled to 5° C. 90 Ml. of chloroformic acid methyl ester are added dropwise while stirring. The mixture is stirred a 5° C. for 30 minutes and at room temperature for 18 hours. Then, the mixture is treated with 100 ml. of methanol and subsequently extracted with 400 ml. of methylene chloride, washed with water, dried over potassium carbonate and evaporated under reduced pressure. Recrystallization of the residue from methanol yields dimethyl 6-[3,6-dihydro-1(2H)-pyridyl]-2,4-pyrimidine-dicarbamate-3-oxide, having a melting point of 202°-203° C.

The last-mentioned 3-oxide can also be prepared as follows:

20 G. of 2,4-diamino-6-[3,6-dihydro-1(2H)-pyridyl]-pyrimidine-3-oxide are suspended and stirred in 100 ml. of methylene chloride and 200 ml. of water. While stirring, there are simultaneously added dropwise 25 ml. of chloroformic acid methyl ester in 50 ml. of methylene chloride and 30 ml. of 28% sodium hydroxide so that the pH value is held between 7.5 and 8.5. After completion of the addition, the suspension is stirred for a further hour and the precipitate formed is subsequently filtered off. The filtrate is washed with methylene chloride and thereafter combined with the precipitate. The whole is recrystallized from methylene chloride/methanol, there being obtained dimethyl 6-[3,6-dihydro-1(2H)-pyridyl]-2,4-pyrimidine-dicarbamate-3-oxide, having a melting point of 202°–206° C. (decomposition).

(B) 56 G. of 2,4-diamino-6-chloropyrimidine-3-oxide in 500 ml. of dimethylformamide and 100 ml. of triethylamine are cooled to 0° C. 80 Ml. of chloroformic acid methyl ester are added dropwise while stirring within 1 hour. After completion of the addition, the mixture is stirred for 48 hours. The precipitate is filtered off, suspended in a mixture of 2500 ml. of methylene chloride and 500 ml. of methanol and stirred for 80 minutes. The insoluble residue is filtered off and dried, there being obtained pure dimethyl 6-chloro-2,4-pyrimidine-dicarbamate-3-oxide, having a melting point of 204° C. (decomposition). The organic phase is washed with water and concentrated, a further amount of pure material being obtained.

A suspension of 10 g. of dimethyl 6-chloro-2,4-pyrimidine-dicarbamate-3-oxide in 40 ml. of methylene chloride is treated with 20 ml. of 1,2,5,6-tetrahydropyridine and stirred at room temperature under an argon atmosphere for 16 hours. The resulting precipitate is filtered off and recrystallized from a mixture of methylene chloride and methanol, there being obtained pure dimethyl 6-[3,6-dihydro-1(2H)-pyridyl]-2,4-pyrimidine-dicarbamate-3-oxide, having a melting point of 203° C.

EXAMPLE 2

Preparation of N-(2'-cyanoacetyl)-1,2,5,6-tetrahydropyridine

83 G. of 1,2,5,6-tetrahydropyridine are mixed under an argon atmosphere with 113 g. of cyanoacetic ester and heated to 110° C., the ethanol formed being distilled off continuously. After 18 hours, the mixture is distilled under reduced pressure, there being obtained N-(2'-cyanoacetyl)-1,2,5,6-tetrahydropyridine, having a melting point of 58°–59° C.

A solution of 25 g. of N-(2'-cyanoacetyl)-1,2,5,6-tetrahydropyridine and 32.2 g. of trimethyloxoniumtetrafluoroborate in 230 ml. of dry methylene chloride is stirred under an argon atmosphere for 20 hours. The mixture is then poured into a cold solution of 31.8 g. of potassium carbonate in 34.5 ml. of water and stirred at 0° C. for 30 minutes. The organic phase is separated, washed with a potassium carbonate solution, dried over potassium carbonate and evaporated under reduced pressure. The residue is dissolved in 150 ml. of ethanol under an argon atmosphere. The solution is treated with 6 g. of cyanamide, stirred overnight and subsequently treated with 5 g. of hydroxylamine hydrochloride and 15 g. of potassium carbonate. The mixture is stirred at room temperature for 35 hours. The precipitated salts are filtered off and washed with ethanol. The filtrate is evaporated and the residue is crystallized from water, there being obtained 2,4-diamino-6-[3,6-dihydro-1(2H)-pyridyl]pyrimidine-3-oxide, having a melting point of 262°–266° C. (decomposition).

EXAMPLE 3

The following compounds were prepared in an analogous manner to that described in Example 1:

(A) from 25 g. of diethyl 6-[3,6-dihydro-1(2H)]-2,4-pyrimidine-dicarbamate-3-oxide, ethyl 5-[3,6-dihydro-1(2H)-pyridyl]-2-oxo-2H-[1,2,4]oxadiazolo[2,3-a]pyrimidine-7-carbamate, having a melting point of 205° C. (decomposition);

(B) from 40.7 g. of diisobutyl 6-[3,6-dihydro-1(2H)-pyridyl]-2,4-pyrimidine-dicarbamate-3-oxide, isobutyl 5-[3,6-dihydro-1(2H)-pyridyl]-2-oxo-2H-[1,2,4]oxadiazolo[2,3-a]pyrimidine-7-carbamate, having a melting point of 201°–203° C. (decomposition);

(C) from 3.1 g. of dibutyl 6-[3,6-dihydro-1(2H)-pyridyl]-2,4-pyrimidine-dicarbamate-3-oxide, butyl 5-[3,6-dihydro-1(2H)-pyridyl]-2-oxo-2H-[1,2,4]oxadiazolo[2,3-a]pyrimidine-7-carbamate, having a melting point of 188°–189° C. (decomposition);

(D) from 8 g. of dioctyl 6-[3,6-dihydro-1(2H)-pyridyl]-2,4-pyrimidine-dicarbamate-3-oxide, octyl 5-[3,6-dihydro-1(2H)-pyridyl]-2-oxo-2H-[1,2,4]oxadiazolo[2,3-a]pyrimidine-7-carbamate, having a melting point of 170° C. (decomposition); and (E) from 10 g. of bis(2-methoxymethyl) 6-[3,6-dihydro-1(2H)-pyridyl]-2,4-pyrimidine-dicarbamate-3-oxide, (2-methoxymethyl) 5-[3,6-dihydro-1(2H)-pyridyl]-2-oxo-2H-[1,2,4]oxadiazolo[2,3-a]pyrimidine-7-carbamate, having a melting point of b 194°–196° C. (decomposition).

The dicarbamates used as the starting materials can be prepared as follows:

(A) 30 G. of 2,4-diamino-6-[3,6-dihydro-1(2H)-pyridyl]pyrimidine-3-oxide in 400 ml. of methylene chloride are mixed with 65 ml. of ethyldiisopropylamine and cooled to 5° C. The mixture is treated while stirring with 70 l ml. of chloroformic acid ethyl ester and stirred at 5° C. for 30 minutes and subsequently at room temperature for 18 hours. The mixture is extracted with 200 ml. of methylene chloride, washed with 200 ml. of water, dried over potassium carbonate and evaporated under reduced pressure. Recrystallization of the residue from ethanol yields diethyl 6-[3,6-dihydro-1(2H)-pyridyl]-2,4-pyrimidine-dicarbamate-3-oxide, having a melting point of 154°–155° C.

(B) 20.7 G. of 2,4-diamino-6-[3,6-dihydro-1(2H)-pyridyl]pyrimidine-3-oxide are mixed with 250 ml. of methylene chloride and 35 ml. of triethylamine and cooled to 5° C. 40 Ml. of chloroformic acid isobutyl ester are added dropwise while stirring. After completion of the addition, the mixture is stirred at 5° C. for 15 minutes and then at room temperature for 2 hours. The solution is treated with 200 ml. of water and extracted with methylene chloride. The organic phase is evaporated and the residue is crystallized from ethanol. There is obtained diisobutyl 6-[3,6-dihydro-1(2H)-pyridyl]-2,4-pyrimidine-dicarbamate-3-oxide, having a melting point of 137°–139° C. (decomposition).

(C) 20 G. of 2,4-diamino-6-[3,6-dihydro-1(2H)-pyridyl]pyrimidine-3-oxide are mixed with 250 ml. of methylene chloride and 35 ml. of triethylamine, stirred and cooled to 5° C. The mixture is treated with 45 ml. of chloroformic acid butyl ester and stirred at room temperature for 6 hours. The mixture obtained is washed with water, extracted with methylene chloride and evaporated under reduced pressure. The residue is recrystallized from ethanol, there being obtained dibutyl 6-[3,6-dihydro-1(2H)-pyridyl]-2,4-pyrimidine-dicarbamate-3-oxide, having a melting point of 131°–132° C.

(D) 10 G. of 2,4-diamino-6-[3,6-dihydro-1(2H)-pyridyl]pyrimidine-3-oxide are suspended in 150 ml. of methylene chloride and 20 ml. of triethylamine. The suspension is cooled to 5° C. and 28 g. of chloroformic acid octyl ester are added dropwise while stirring. The mixture is cooled for 30 minutes and then stirred at room temperature for 1 hour. The mixture is extracted with methylene chloride, washed with water, dried over magnesium sulfate and evaporated under reduced pressure. The residue is recrystallized from methylene chloride/ethanol, there being obtained dioctyl 6-[3,6-dihydro-1(2H)-pyridyl]-2,4-pyrimidine-dicarbamate-3-oxide, having a melting point of 64° C.

(E) 10 G. of 2,4-diamino-6-[3,6-dihydro-1(2H)-pyridyl]-pyrimidine-3-oxide are stirred at 5° C. in 150 ml. of methylene chloride and 30 ml. of triethylamine and treated with 20 ml. of chloroformic acid 2-methoxyethyl ester. The mixture is stirred at room temperature for 4 hours, then washed with water and extracted with methylene chloride. The organic phases are evaporated under reduced pressure and the residue is recrystallized from diethyl ether, there being obtained bis(2-methoxyethyl) 6-[3,6-dihydro-1(2H)-pyridyl]-2,4-pyrimidine-dicarbamate-3-oxide, having a melting point of 126°–128° C.

EXAMPLE 4

Preparation of methyl 5-[3,6-dihydro-1(2H)-pyridyl]-2-oxo-2H-[1,2,4]oxadiazolo[2,3-a]-pyrimidine-7-carbamate 32.3 G. of dimethyl 6-[3,6-dihydro-1(2H)-pyridyl]-2,4-pyrimidine-dicarbamate-3-oxide are stirred at room temperature for 3 hours in a mixture of methylene chloride and 3% sodium hydroxide. The two phases are separated and the aqueous phase is made acid, there being obtained methyl 5-[3,6-dihydro-1(2H)-pyridyl]-2-oxo-2H-[1,2,4]oxadiazolo[2,3-a]-pyrimidine-7-carbamate, having a melting point of 210°–212° C.

EXAMPLE 5

Preparation of dibutyl 6-[3,6-dihydro-1(2H)-pyridyl]-2,4-pyrimidine-dicarbamate-3-oxide and butyl 5-[3,6-dihydro-1(2H)-pyridyl]-2-oxo-2H-[1,2,4]oxadiazolo[2,3-a]pyrimidine-7-carbamate 2.0 G. of methyl 5-[3,6-dihydro-1(2H)-pyridyl]-2-oxo-2H-[1,2,4]oxadiazolo[2,3-a]pyrimidine-7-carbamate are heated to reflux in 100 ml. of n-butanol with 50 mg. of sodium under an atmosphere of argon. After 6 hours, the solution is made acid with hydrochloric acid and evaporated. After chromatographic separation, there are obtained dibutyl 6-[3,6-dihydro-1(2H)-pyridyl]-2,4-pyrimidine-dicarbamate-3-oxide, having a melting point of 126°–128° C. and butyl 5-[3,6-dihydro-1(2H)-pyridyl]-2-oxo-2H-[1,2,4]oxadiazolo[2,3-a]pyrimidine-7-carbamate, having a melting point of 183°–187° C.

EXAMPLE 6

Preparation of diisobutyl 6-[3,6-dihydro-1(2H)-pyridyl]-2,4-pyrimidine-dicarbamate 3-oxide and isobutyl 5-[3,6-dihydro-1(2H)-pyridyl]-2-oxo-2H-[1,2,4]oxadiazolo[2,3-a]-pyrimidine-7-carbamate 3 G. of dimethyl 6-[3,6-dihydro-1(2H)-pyridyl]-2,4-pyrimidine-dicarbamate-3-oxide are heated to reflux under an atmosphere of argon with 100 mg. of potassium carbonate in 100 ml. of isobutanol. The mixture is cooled, made acid with hydrochloric acid and the solvent is evaporated. The residue is extracted with chloroform and washed with water. The organic solution is dried over magnesium sulfate and evaporated under reduced pressure. The residue is chromatographed over silica gel, there being obtained diisobutyl 6-[3,6-dihydro-1(2H)-pyridyl]-2,4-pyrimidine-dicarbamate-3-oxide and isobutyl 5-[3,6-dihydro-1(2H)-pyridyl]-2-oxo-2H-[1,2,4]oxadiazolo[2,3-a]pyrimidine-7-carbamate, having a melting point of 201°–203° C.

EXAMPLE 7

Preparation of the 3-azabicyclo[3.2.2]nonane salt of methyl 5-[3,6-dihydro-1(2H)-pyridyl]-2-oxo-2H-[1,2,4]oxadiazolo[2,3-a]pyrimidine-7-carbamate 2 G. of methyl 5-[3,6-dihydro-1(2H)-pyridyl]-2-oxo-2H-[1,2,4]oxadiazolo[2,3-a]-pyrimidine-7-carbamate are suspended in acetonitrile and treated with 1.6 g. of 3-azabicyclo[3.2.2]nonane in 20 ml. of acetonitrile. There is first obtained a clear solution, but there very rapidly precipitates out the corresponding 3-azabicyclo[3.2.2]nonane salt, the structure of which was confirmed by X-ray structural analysis. The pure salt having a melting point of 164°–168° C. is obtained by recrystallization.

EXAMPLE 8

Preparation of the sodium salt of methyl 5-[3,6-dihydro-1(2H)-pyridyl]-2-oxo-2H-[1,2,4]oxadiazolo[2,3-a]-pyrimidine-7-carbamate 3 G. of methyl 5-[3,6-dihydro-1(2H)-pyridyl]-2-oxo-2H-[1,2,4]oxadiazolo[2,3-a]-pyrimidine-7-carbamate are dissolved in 2-N sodium hydroxide and the solution is left to stand. Upon cooling there precipitates out the corresponding sodium salt which is recrystallized from acetonitrile and water and which begins to decompose from 145° C.

The following Examples illustrate pharmaceutical preparations containing the oxadiazolopyrimidine derivatives provided by the present invention:

EXAMPLE A

Tablets containing the following ingredients are prepared:

| | | |
|---|---|---|
| I | Methyl 5-[3,6-dihydro-1(2H)-pyridyl]-2-oxo-2H-[1,2,4]oxadiazolo[2,3,-a]-pyrimidine-7-carbamate (micronized) | 20.0 mg. |
| | Lactose (powdered) | 40.0 mg. |
| | Maize starch (white) | 24.9 mg. |
| II | Dioctyl sodium sulfosuccinate | 0.1 mg. |
| | Maize starch (white) | 5.0 mg. |
| | Water | q.s. |
| III | Maize starch (white) | 6.0 mg. |
| IV | Talc | 3.0 mg. |
| | Magnesium stearate | 1.0 mg. |
| | | 100.0 mg. |

The ingredients of phase I are sieved and mixed. The mixture is moistened with the maize starch paste, phase II, and kneaded. The moist mass is granulated, dried and converted into a suitable granular size. Phase III is admixed. The resulting mixture is mixed with Phase IV for a further short time. The ready-to-press mixture is pressed to tablets weighing 100 mg, having a diameter of 7 mm. and having a break-bar.

EXAMPLE B

Tablets containing the following ingredients are prepared:

| | | |
|---|---|---|
| I | Methyl 5-[3,6-dihydro-1(2H)-pyridyl]-2-oxo-2H-[1,2,4]oxadiazolo[2,3-a]-pyrimidine-7-carbamate (micronized) | 200.0 mg. |
| | Lactose (powdered) | 42.9 mg. |
| | Maize starch (white) | 50.0 mg. |
| II | Dioctyl sodium sulfosuccinate | 0.1 mg. |
| | Maize starch (white) | 20.0 mg. |
| | Water | q.s. |
| III | Maize starch (white) | 30.0 mg. |
| IV | Talc | 3.5 mg. |
| | Magnesium stearate | 3.5 mg. |
| | | 350.0 mg. |

The ingredients of Phase I are sieved and mixed. The mixture is moistened with the maize starch paste, phase II, and kneaded. The moist mass is granulated, dried and converted into a suitable granular size. Phase III is admixed. The resulting mixture is mixed with phase IV for a further short time. The ready-to-press mixture is pressed to tablets weighing 350 mg., having a diameter of 11 mm and having a break-bar.

EXAMPLE C

Capsules containing the following ingredients are prepared:

| | | |
|---|---|---|
| I | Methyl 5-[3,6-dihydro-1(2H)-pyridyl]-2-oxo-2H-[1,2,4]oxadiazolo[2,3-a]-pyrimidine-7-carbamate (micronized) | 20.0 mg. |
| | Lactose (powdered) | 48.0 mg. |
| II | Maize starch | 5.0 mg. |
| | Water | q.s. |
| III | Lactose (crystalline) | 50.0 mg. |
| | Maize starch | 15.0 mg. |
| IV | Talc | 10.0 mg. |
| | Magnesium stearate | 2.0 mg. |
| | | 150.0 mg. |

The ingredients of phase I are sieved and mixed. The mixture is moistened with the maize starch paste, phase II, and kneaded. The moist mass is granulated, dried and converted into a suitable granular size. Phase III is admixed. The resulting mixture is mixed with phase IV for a further short time. The mixture obtained is filled into capsules (size 2) each containing 150 mg.

EXAMPLE D

Capsules containing the following ingredients are prepared:

| | | |
|---|---|---|
| I | Methyl 5-[3,6-dihydro-1(2H)-pyridyl]-2-oxo-2H-[1,2,4]oxadiazolo[2,3-a]-pyrimidine-7-carbamate (micronized) | 200.0 mg. |
| | Lactose (powdered) | 50.0 mg. |
| II | Maize starch | 15.0 mg. |
| | Water | q.s. |
| III | Lactose (crystalline) | 50.0 mg. |
| | Maize starch | 20.0 mg. |
| IV | Talc | 10.0 mg. |
| | Magnesium stearate | 5.0 mg. |
| | | 350.0 mg. |

The ingredients of phase I are sieved and mixed. The mixture is moistened with the maize starch paste, phase II, and kneaded. The moist mass is granulated, dried and converted into a suitable granular size. Phase III is admixed. The resulting mixture is mixed with phase IV for a further short time. The mixture obtained is filled into capsules (size 1) each containing 350 mg.

EXAMPLE E

An aqueous drop suspension containing the following ingredients is prepared:

| | 10 mg. per 1 ml. |
|---|---|
| Methyl 5-[3,6-dihydro-1(2H)-pyridyl]-2-oxo-2H-[1,2,4]oxadiazolo[2,3-a]-pyrimidine-7-carbamate (micronized) | 0.1 g. |
| Sodium benzoate | 0.035 g. |
| Sodium saccharin | 0.015 g. |
| Acrylic acid polymerizate | 0.1–1.0 g. |
| Saccharose | 3.5 g. |
| Citric acid | 0.025 g. |
| Polyoxyethylene stearate | 0.002–0.01 g. |
| Sodium hydroxide | q.s. |
| Aroma | q.s. |
| Foodstuff colorant | q.s. |
| Deionized water | ad 10.0 ml. |

EXAMPLE F

An aqueous drop suspension containing the following ingredients is prepared:

| | 100 mg. per 1 ml. |
|---|---|
| Methyl 5-[3,6-dihydro-1(2H)-pyridyl]-2-oxo-2H-[1,2,4]oxadiazolo[2,3-a]-pyrimidine-7-carbamate (micronized) | 1.0 g. |
| Sodium benzoate | 0.035 g. |
| Sodium saccharin | 0.015 g. |
| Acrylic acid polymerizate | 0.05–0.5 g. |
| Saccharose | 3.5 g. |
| Citric acid | 0.025 g. |
| Polyoxyethylene stearate | 0.002–0.01 g. |
| Sodium hydroxide | q.s. |
| Aroma | q.s. |
| Foodstuff colorant | q.s. |
| Deionized water | ad 10.0 ml. |

We claim:

1. A compound of the formula

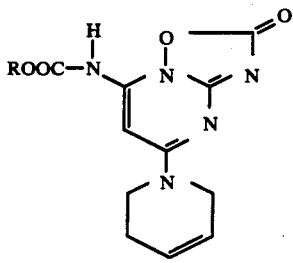

wherein R is alkyl or alkoxyalkyl, or a salt thereof with a pharmaceutically acceptable base.

2. A compound in accordance with claim 1, wherein R is alkyl.

3. A compound in accordance with claim 2, wherein R is alkyl of 1-4 carbon atoms.

4. A compound in accordance with claim 1, methyl 5-[3,6-dihydro-1(2H)-pyridyl]-2-oxo-2H-[1,2,4]oxadiazolo[2,3-a]pyrimidine-7-carbamate.

5. A compound in accordance with claim 1, ethyl 5-[3,6-dihydro-1(2H)-pyridyl]-2-oxo-2H-[1,2,4]oxadiazolo[2,3-a]pyrimidine-7-carbamate.

6. A compound in accordance with claim 1, isobutyl 5-[3,6-dihydro-1(2H)-pyridyl]-2-oxo-2H-[1,2,4]oxadiazolo[2,3-a]pyrimidine-7-carbamate.

7. A compound in accordance with claim 1, butyl 5-[3,6-dihydro-1(2H)-pyridyl]-2-oxo-2H-[1,2,4]oxadiazolo[2,3-a]pyrimidine-7-carbamate.

8. A compound in accordance with claim 1, octyl 5-[3,6-dihydro-1(2H)-pyridyl]-2-oxo-2H-[1,2,4]oxadiazolo[2,3-a]pyrimidine-7-carbamate.

9. A compound in accordance with claim 1, (2-methoxyethyl) 5-[3,6-dihydro-1(2H)-pyridyl]-2-oxo-2H-[1,2,4]oxadiazolo[2,3-a]pyrimidine-7-carbamate.

10. A pharmaceutical composition comprising a compound of the formula

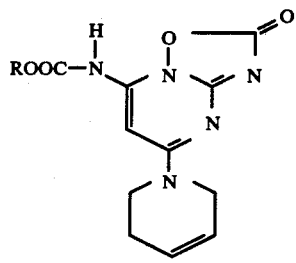

wherein R is alkyl or alkoxyalkyl, or a salt thereof with a pharmaceutically acceptable base and a compatible pharmaceutical carrier material.

* * * * *